United States Patent
Dal Farra et al.

(10) Patent No.: US 8,188,050 B2
(45) Date of Patent: May 29, 2012

(54) PHARMACEUTICAL AND/OR COSMETIC COMPOSITION CONTAINING PEPTIDES

(75) Inventors: Claude Dal Farra, Opio (FR); Nouha Domloge, Valbonne (FR); Jean-Marie Botto, Valbonne (FR)

(73) Assignee: ISP Investments Inc., Wilmington, DE (US)

( * ) Notice: Subject to any disclaimer, the term of this patent is extended or adjusted under 35 U.S.C. 154(b) by 387 days.

(21) Appl. No.: 12/446,951

(22) PCT Filed: Oct. 26, 2007

(86) PCT No.: PCT/FR2007/001774
§ 371 (c)(1),
(2), (4) Date: Apr. 23, 2009

(87) PCT Pub. No.: WO2008/059127
PCT Pub. Date: May 22, 2008

(65) Prior Publication Data
US 2010/0152119 A1    Jun. 17, 2010

(30) Foreign Application Priority Data

Oct. 26, 2006  (FR) ..................................... 06 09415

(51) Int. Cl.
*A61K 38/00* (2006.01)
*A61K 38/08* (2006.01)
*A61K 38/06* (2006.01)
*A61K 38/07* (2006.01)
*A61P 17/00* (2006.01)

(52) U.S. Cl. ...................... 514/18.6; 514/21.7; 514/21.9
(58) Field of Classification Search .................. None
See application file for complete search history.

(56) References Cited

U.S. PATENT DOCUMENTS 6,329,501 B1 * 12/2001 Smith et al. .................. 530/329

FOREIGN PATENT DOCUMENTS

| WO | WO 03/022995 | * | 3/2003 |
| WO | WO 2004/016653 | * | 2/2004 |

OTHER PUBLICATIONS

Rebecca L. Lamason et al. "SLC24A5, a Putative Cation Exchanger, Affects Pigmentation in Zebrafish and Humans", Science, American Association for the Advancement of Science, US, vol. 310, No. 5755, Dec. 2005, pp. 1782-1786, 1778, XP002409124, ISSN: 0036-8075.
International Search Report mailed Apr. 21, 2008.

* cited by examiner

*Primary Examiner* — Marcela M Cordero Garcia
(74) *Attorney, Agent, or Firm* — Young & Thompson

(57) ABSTRACT

The present invention concerns the use of peptide fragments of the protein SLC24A5 as active agents designed to induce, increase, or restore the synthesis of melanin in the melanocytes of the epidermis or of the pilar bulb, alone or in association with at least one other active agent, in a cosmetic composition or for the preparation of a pharmaceutical or particularly dermatological composition. The invention is also related to any composition containing the active agents.

20 Claims, No Drawings

```
                        SEQUENCE LISTING

<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Gly Gly Leu Thr Leu Leu Ala Ala
1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 2

Leu Thr Leu Leu Ala Ala
1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Thr Leu Leu Ala
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Thr Val Phe Ala
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Thr Ala Leu Ala
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Thr Val Leu Ala
1
```

PHARMACEUTICAL AND/OR COSMETIC COMPOSITION CONTAINING PEPTIDES

The present invention is in the cosmetic and pharmaceutical domain, and more particularly in the domain of dermatology. The present invention concerns the use of peptide fragments of the protein SLC24A5, as active agents, alone or in association with at least one other active agent in a cosmetic composition or for the preparation of a pharmaceutical and particularly a dermatological composition. The said active agents are designed to induce, increase, or restore the synthesis of melanin in the melanocytes of the epidermis or the pilar bulb, with a view to giving the skin a bronzed appearance, to preparing it for exposure to the sun, or to protecting it from ultraviolet (UV) radiation. The said active agents can also be used for therapeutic ends, to prepare a pharmaceutical composition designed to repigment skin depigmented, for example, in the case of vitiligo or to pigment fur or hair, in particular in the treatment and the prevention of canities. The invention is also related to any composition containing the said active component.

In the human being, the color of the hair and of the skin is linked to individual factors (ethnic origin, sex, age, etc.) and to environmental factors (particularly, the seasons of the year, the zone of habitation, etc.) It is principally determined by nature and the concentration of melanin produced by the melanocytes. Melanin has the property of protecting the cutaneous cells from the deleterious effects of UV radiation and of slowing down cutaneous photo-aging. The melanocytes are specialized cells which, by the intermediary of specific organelles, the melanosomes, synthesize melanin. The synthesis of melanin, or melanogenesis, is a complex process whose precise mechanisms are still not fully clarified and which causes the following stages, represented schematically, to occur:

Tyrosine-->DOPA-->Dopaquinone-->Dopachrome-->Melanin

In the epidermis, the melanocyte is involved in the epidermal melanic unit which includes one melanocyte surrounded by about 40 neighboring keratinocytes. As melanin is synthesized in the melanosomes, these are displaced from the perinuclear region toward the end of the melanocyte dendrites. Through phagocytosis, the end of the dendrites is captured by the keratinocytes, the membranes damaged, and the melanosomes redistributed in the keratinocytes, where they will provide protection up until the natural desquamation of the cells. The production of melanin, as well as its transport, is regulated by various factors such as, for instance, UV radiation, hormones, or chemical products. Thus, an increase in exposure to UV radiation causes the synthesis of pigments and the tanning of the skin, which has the effect of protecting the skin from UV radiation.

The natural pigmentation of hair and fur by melanin requires the presence of melanocytes at the level of the bulb of the hair follicle. The hair follicle is a tubular invagination of the epidermis which is embedded as far as the deep layers of the dermis. The melanocytes at the level of the hair-follicle bulb are in an active state, that is, they synthesize melanin. These pigments are conveyed to keratinocytes destined to form the pilar stem, which will lead to the growth of a pigmented hair or fur.

It is accepted that canities (natural whitening of the hair) is associated with a reduction in melanin in the pilar stem.

The search for compounds able to promote the synthesis of melanin in the skin and the hair in the absence of UV stimulation is a concern of dermatology and cosmetics. These new compounds would be particularly useful as an alternative to exposure to the sun, to prepare the skin and protect it from the sun's rays, to obtain a more intense tanning after exposure to the sun, to prolong the natural pigmentation of the skin after exposure to the sun, or to prevent and/or limit and/or stop the development of canities and even maintain the natural pigmentation in grey or white hair and/or fur.

Natural pigmentation of the skin is understood to be the coloration of the skin or the hair determined by the concentration of melanin.

Fur or hair is understood to be the collection of pilar appendages and particularly the eyelashes and eyebrows.

In this respect, numerous solutions have been proposed, by introducing exogenous colorants, the best known of which is dihydroxyacetone or DHA. However, only the stimulation of the pigmentation of the skin and/or the hair by natural means permits real protection with respect to UV radiation, and it remains the ideal way to stimulate pigmentation. Thus, the preparation and use of melanin-biosynthesis activators have been proposed in prior art (FR 828097, FR 2831438, FR 2845285), which cause hormones (alpha melanocyte-stimulating hormone ($\alpha$-MSH) or its derivatives, WO 2006037188) or prostaglandins (WO 9511003) to intervene.

On the other hand, the use of compounds promoting the synthesis of melanin in the skin and the hair is very particularly interesting in treating the pathologies causing localized under-pigmentations of origins which are genetic, autoimune like vitiligo, due to aging, or even post-lesional (scars, mycoses).

The principal objective of the present invention is to provide a new active agent capable of inducing, increasing, or restoring melanin synthesis in the melanocytes of the epidermis and the pilar bulb. The inventors have indeed highlighted a therapeutic and more particularly a dermatological and cosmetic activity of peptide fragments of the protein SLC24A5. It has been particularly highlighted that these proteins and/or peptide fragments, when they are applied to the skin, promote in a significant way the synthesis of melanin in the melanocytes of the epidermis or of the pilar bulb. These new active agents thus enable new therapeutic and cosmetic perspectives to be opened up.

The protein SLC24A5 was recently discovered in mutant zebra fish which exhibited a skin lighter than the set of individuals of the same species (Lamason, R. et. al. (2005), Science, 310(5755), 1782-6). The mutant zebra fish possess a variant form of the protein associated with the presence in their skin of melanosomes which are less numerous, smaller, and lighter in color. The studies conducted on this fish have enabled the SLC24A5 protein to be localized in the membrane of the melanosomes and a probable function attributed to it of an ion-exchange channel for sodium/calcium ions. The role of the SLC24A5 protein in the coloration of the human skin seems to be a determining factor, since the polymorphism recognized in the human gene, which is manifested respectively by the presence of an alanine or a threonine, is split up in a very differentiated way according to the phenotypes of skin color. Thus, the alanine allele has a frequency of 93% among Africans, while the threonine allele is found in 98-100% of Europeans.

To date, no use of the SLC24A5 protein has been described in cosmetic or pharmaceutical compositions.

Thus, the invention has, as a first object, the use of peptide fragments or the biologically active derivatives of them, as active agents, alone or in association with at least one other active agent, in a cosmetic composition or for the preparation of a pharmaceutical and/or dermatological composition.

Preferentially, according to the present invention, the said peptide fragments of the SLC24A5 protein or their biologically active derivatives are peptide fragments whose number of amino acids is between 4 and 50, and more particularly between 4 and 8. All these peptide fragments possess a biological activity.

According to a particularly advantageous embodiment of the invention, the peptide possesses a sequence which answers in whole or in part to the general formula (I):

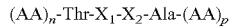

in which
X$_1$ is any aliphatic amino acid (Leu or Ile or Val or Ala)
X$_2$ is phenylalanine or leucine and where
AA represents any amino acid or one of its derivatives, and n and p are whole numbers between 0 and 4.

According to one very particularly preferred embodiment of the invention, the active peptide fragment is a peptide of sequence:

| | |
|---|---|
| Gly-Gly-Leu-Thr-Leu-Leu-Ala-Ala | (SEQ ID No. 1) |
| Leu-Thr-Leu-Leu-Ala-Ala | (SEQ ID No. 2) |
| Thr-Leu-Leu-Ala | (SEQ ID No. 3) |
| Thr-Val-Phe-Ala | (SEQ ID No. 4) |
| Thr-Ala-Leu-Ala | (SEQ ID No. 5) |
| Thr-Val-Leu-Ala | (SEQ ID No. 6) |

According to one particularly interesting embodiment, the active peptide corresponds to the sequence SEQ ID No. 3.

According to another particularly interesting embodiment, the active peptide corresponds to the sequence SEQ ID No. 4.

The invention also concerns variant forms of these sequences and/or these fragments. The term "variant" here refers to a peptide that differs, for example, from the sequence of a reference peptide while still retaining its essential properties. Generally, the differences are limited in such a way that the sequences of the reference peptide and those of the variant are quite similar and, in some regions, identical.

Preferentially, the variant forms are those which vary from the reference sequences by the substitution of chemically equivalent amino acids (or homologues), that is, by the substitution of one residue by another one possessing the same characteristics. Thus, the classic substitutions are between Ala, Val, Leu, and Ile; between Ser and Thr, between the acidic Asp and Glu residues, between Asn and Gln, and between the basic Lys and Arg residues, or between the aromatic Phe and Tyr residues. The term "variant" thus refers to a peptide that differs, for instance, in sequence from the reference peptide while still retaining its essential properties. Generally, the differences are limited in such a way that the sequences of the reference peptide and those of the variant are quite similar and, in some regions, identical. A variant peptide and a reference peptide may thus differ in the sequence of amino acids by one or several substitutions, additions, or deletions in any combination.

The use of the described fragments of the SLC24A5 protein in the present invention also includes the use of any biological active fragments or of one their analogues or variants.

The expression "biologically active" is understood to be "which has an in vivo or in vitro activity characteristic of the activity of the active agent according to the invention", that is, the property of inducing, increasing, or restoring the synthesis of melanin in the melanocytes. Thus, a variant peptide according to the invention will be obtained by one or several substitutions of chemically equivalent amino acids and will exhibit the property of inducing, increasing, or restoring the synthesis of melanin in the melanocytes, with an effectiveness similar to that of a peptide of general formula (I).

In the invention, the term "amino acid" refers here to any natural or non-natural organic acid having the formula:

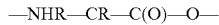

where each —R is selected independently from a hydrogen and an alkyl group having between 1 and 12 carbon atoms. Preferentially, at least one group —R of each amino acid is a hydrogen. The term "alkyl" is understood here to be a carbon chain which can be linear or branched, substituted (mono- or poly-) or un-substituted; saturated, mono-saturated (a double or triple bond in the chain) or poly-unsaturated (two or several double bonds, two or several triple bonds, one or several double bonds and one or several triple bonds in the chain).

The term "peptide" means a chain of two or several amino acids linked to each other by peptide bonds or by modified peptide bonds.

A "peptide" is to be understood as the natural or synthetic peptide of the invention as described above or at least one of its fragments, which might be obtained by proteolysis or synthetically, or even any natural or synthetic peptide whose sequence is wholly or partially composed of the sequence of the peptide described previously.

So as to improve resistance to damage, it may be necessary to use a protected form of the peptide according to the invention. The form of protection should of course be a biologically compatible form and should be compatible with a use in the domain of cosmetics or pharmaceuticals.

Numerous forms of biologically compatible protection may be envisioned; they are well known to the professional person, such as, for example, the acylation or the acetylation of the amino-terminal end or the amidation or the esterification of the carboxy-terminal end. Thus, the invention concerns a use as defined previously characterized by the fact that the peptide is in a protected form or not. Preferably, protection is used which is based either on the acylation or the acetylation of the amino-terminal end, or on the amidation or the esterification of the carboxy-terminal end, or even on both of these two. The amino acid derivatives and the peptide derivatives also concern amino acids and peptides connected to one another by a pseudo-peptide bond. A "pseudo-peptide bond" is understood to be any of the types of bond likely to replace the "classic" peptide bonds.

In the domain of the amino acids, the geometry of the molecules is such that they can theoretically exhibit the form of different optical isomers. Indeed, there exists one molecular conformation of the amino acid (AA) such that it deflects the plane of light polarization to the right (dextrorotatory or D-aa conformation), and there is another molecular conformation of the amino acid (aa) such that it deflects the plane of light polarization to the left (levorotatory or L-aa conformation). In nature, only the levorotatory conformation is retained in natural amino acids. Consequently, a peptide of natural origin will only be composed of amino acids of L-aa type. However, chemical synthesis in the laboratory enables amino acids to be prepared which have both possible conformations.

Starting with this material as a base, it is thus possible during peptide synthesis to incorporate equally well amino acids in the form of dextrorotatory optical isomers or levorotatory. Thus, the amino acids composing the peptide according to the invention may be in the L or D configuration; preferentially, the amino acids are in the L form. The peptide according to the invention can thus be in an L, D, or DL form.

The peptide, the object of the present patent, can be obtained either by classical chemical synthesis (in solid phase or homogeneous liquid phase) or by enzymatic synthesis (Kullman et al. (1980), *J. Biol. Chem.* 225, 8234), starting from the constituent amino acids or their derivatives.

The peptide according to the invention can also be obtained by fermentation of a strain of bacteria, modified or not by genetic engineering to produce the peptides of general formula (I), or even by extraction of proteins of animal or vegetable origin, preferentially of vegetable origin, followed by a controlled hydrolysis, which liberates the peptide fragments of moderate and small size, the object of the invention.

A great many proteins found in plants are likely to contain these sequences within their structure. Controlled hydrolysis enables these peptide fragments to be released. It is possible, but not necessary to achieve the invention, either to extract the proteins concerned first and then to hydrolyze them, or to perform the hydrolysis first on a raw extract and to subsequently purify the peptide fragments. It is also possible to use certain hydrolyzed extracts without purifying the peptide fragments in them according to the invention, but while ensuring at the same time the presence of the said fragments by appropriate analytical means.

Other procedures, simpler or more complex, may be envisioned by the professional familiar with the craft of the synthesis, extraction, and purification of proteins and peptides. Thus, the peptide according to the invention can be of natural or synthetic origin. Preferentially, according to the invention, the peptide is obtained by chemical synthesis.

In the composition according to the invention, the peptides can be a mixture of peptide derivatives and/or be composed of amino acid derivatives.

According to one advantageous embodiment of the invention, the peptide fragments of the SLC24A5 protein with general formula (I) are solubilized in advance in one or several cosmetically or pharmaceutically acceptable solvents traditionally used by the professional, such as water, glycerol, ethanol, propylene glycol, butylene glycol, dipropylene glycol, ethoxylated or propoxylated diglycols, cyclic polyols, vaseline, a vegetable oil, or any mixture of these solvents.

According to yet another advantageous embodiment of the invention, the peptides with general formula (I) are solubilized in advance in a cosmetic or pharmaceutical vehicle like the liposomes or are adsorbed onto powdered organic polymers or mineral supports like the talcs and bentonites, and are more generally solubilized in, or fixed upon, any cosmetically or pharmaceutically acceptable vehicle.

Naturally, the peptide according to the invention can be used, as an active agent, alone or even in association with at least one other active agent, in or for the preparation of a cosmetic and/or dermatological and/or pharmaceutical composition.

In the composition according to the invention, the peptide can be a mixture of peptide derivatives and/or composed of amino acid derivatives.

The compositions according to the invention can be applied in any appropriate way, particularly oral, parenteral, or external topical, and their formulation will be adapted by the professional, specifically for cosmetic or dermatological compositions. Advantageously, the compositions according to the invention are intended for administration by a topical cutaneous means. They contain a physiologically acceptable medium, a medium acceptable, specifically cosmetologically or pharmaceutically, and particularly dermatologically, and cover all the cosmetic or dermatological forms. These compositions should therefore contain a cosmetically and/or dermatologically acceptable medium, that is, one compatible with the skin, the fur, or the hair. These compositions can particularly be in the form of creams, oil-in-water or water-in-oil emulsions, or multiple emulsions, solutions, suspensions, gels, milks, lotions, sticks, or even powders, adapted to an application onto the skin, the lips, and/or the hair.

These compositions include the excipients necessary for their formulation, such as solvents, thickeners, diluents, surfactants, antioxidants, colorants, preservatives, or perfumes.

Of course, the professional will take care to choose possible further compounds, active or inactive, and/or their quantity, in such a way that the advantageous properties of the mixture are not, or are not essentially, altered by the addition envisioned.

The composition usable according to the invention can, in particular, consist of a composition for hair care, and particularly a shampoo, a conditioner, a blow-dry lotion, a treatment lotion, a cream or a styling gel, a restructuring lotion for the hair, a mask, etc. The cosmetic composition according to the invention can be used particularly in treatments implementing an application that is followed or not followed by a rinse, or even in the form of shampoo.

It can also come in the form of a dye or mascara to be applied with the brush or the comb, in particular on the eyelashes, eyebrows, or hair.

Advantageously, the compositions usable according to the invention contain in addition at least one other agent promoting the pigmentation of the skin, hair, and/or fur.

Such compounds are, particularly, substrates of tyrosinase, such as tyrosine or L-DOPA, prostaglandins, or activator compounds by the route of cyclic adenosine 3',5'-monophosphate (cAMP) such as pro-opiomelanocortin derivatives, adenosine, or forskolin or its derivatives. Plant extracts may also be cited, such as the Seville orange (*Citrus aurantium*) or the chrysanthemum (*Chrysanthemum morifolium*), described particularly in the patents FR 2845285 and EP 1014934.

Such compounds are also found in the family of exogenous colorants of the surface layers of the epidermis, such as dihydroxyacetone (DHA), erythrulose, and the extracts of henna leaves, described particularly in the patents EP 0742002 and FR 2779958.

It is quite obvious that the invention is directed toward mammals in general and more particularly toward human beings.

The effective amount of active agent corresponds to the quantity necessary to obtain the desired result. According to an advantageous embodiment of the invention, the aforementioned peptide is present in the compositions of the invention in a concentration approximately between 0.0005 and 500 ppm (parts per million), and preferentially in a concentration approximately between 0.01 and 5 ppm, relative to the total weight of the final composition.

These compositions can come particularly in the form of an aqueous, hydroalcoholic, or oily solution, an oil-in-water or water-in-oil emulsion, or multiple emulsions. They can also come in the form of creams, suspensions, or even powders, adapted to an application onto the skin, the mucous membranes, the lips, and/or the appendages of the skin. These compositions can be more or less fluid and have the appearance of a cream, a lotion, a milk, a butter, an ointment, a gel, a paste, or a mousse. They can also come in solid form like a stick or be applied on the skin in the form of an aerosol. They can be used as a care product and/or as a makeup product for the skin.

These compositions include, in addition, any additive commonly used in the domain of application envisioned, as well as the adjuvants necessary for their formulation, such as solvents, thickeners, diluents, antioxidants, colorants, solar filters, self-tanning agents, pigments, vehicles, preservatives, perfumes, odor absorbents, active cosmetic or pharmaceutical components, essential oils, vitamins, essential fatty acids, surfactants, film-forming polymers, etc.

In any case, the professional will take care that these adjuvants, as well as their proportions, are chosen in such a way as not to harm the advantageous properties studied in the composition according to the invention. These adjuvants can, for instance, correspond to 0.01 to 20% of the total weight of the composition. When the composition of the invention is an emulsion, the fatty phase can represent 5 to 80% by weight and preferably 5 to 50% by weight relative to the total weight of the composition. The emulsifiers and co-emulsifiers used in the composition will be chosen from among those traditionally used in the domain considered. For example, they can be used in a proportion from 0.3 to 30% by weight relative to the total weight of the composition.

Another object of the invention consists of a cosmetic or pharmaceutical composition characterized by the fact that it contains, in a physiologically acceptable medium, the active agent according to the invention, in order to prepare the skin for exposure to the sun and to protect it from solar radiation.

The invention consists, once again, of a pharmaceutical composition characterized by the fact that the active agent according to the invention is formulated to alleviate a pathology linked to pigmentation such as vitiligo which is manifested by a localized under-pigmentation of the skin.

The invention also has, as an object, use in a cosmetic composition or for preparing a pharmaceutical composition with an effective quantity of active agent as described previously, that is, one or several peptide fragments of the protein SLC24A5 possessing a sequence that answers in whole or in part to the general formula (I).

These peptides correspond in an advantageous way to the sequences SEQ ID No. 1 to No. 6.

According to a particularly advantageous embodiment of the invention, these peptides correspond to the sequences SEQ ID No. 3 and No. 4.

The invention also has, as an object, use in a cosmetic composition or for preparing a pharmaceutical composition with an effective quantity of active agent as described previously, the active agent or the composition containing it being designed to induce, restore, or stimulate the natural pigmentation of the skin, fur, or hair.

The invention again is related to use in a cosmetic composition or for preparing a pharmaceutical composition with an effective quantity of active agent as described previously, the active agent or the composition containing it being designed to prepare the skin for exposure to the sun.

The invention again is related to use in a cosmetic composition or for preparing a pharmaceutical composition with an effective quantity of active agent as described previously, the active agent or the composition containing it being designed, by increasing the synthesis of melanin, to protect the skin from solar radiation.

The invention again is related to use in a cosmetic composition or for preparing a pharmaceutical composition with an effective quantity of active agent as described previously, the active agent or the composition containing it being designed to improve the intensity and/or the homogeneity and/or the durability of the pigmentation of the skin and/or of the hair.

The invention has, in addition, as an object, the use of at least one active agent as defined previously, in or for the preparation of a cosmetic or pharmaceutical composition, the active agent or the composition containing it being designed to protect the skin and its appendages from stresses that the environment produces upon them. More precisely, the present invention aims for the use of at least one active agent as defined previously to protect the skin and/or its appendages against all types of external aggression. The term "external aggression" is understood to mean aggressions that the environment generates. These aggressions may be of chemical, physical, biological, or thermal origin. By way of example, aggressions by such means as pollution, UV radiation, friction, hard water, variations in temperature, or even products of an irritant nature such as surfactants, preservatives, or perfumes, may be cited.

Appendages of the skin are understood to be the collection of tegumentary appendages and particularly the nails, the fur, and the hair. Fur and hair are understood to be the assemblage of pilar appendages, and in particular the eyelashes and eyebrows as well.

In addition, the peptides according to the invention, or the composition containing them, have anti-inflamatory and anti-irritant effects. The use of the properties of this cosmetic agent therefore allows skin to be more protected and clearly less sensitive to various aggressions that it may encounter. The skin is thus soothed.

The peptides coming from the family of the SLC24A5 protein and possessing the general formula (I) are thus used to fabricate a pharmaceutical composition for topical usage. They will be used in a more specific way to treat the dermatological conditions linked to pigmentation. In this relation, pathologies like vitiligo may be cited, which is an autoimmune disease characterized by the appearance on the skin of white patches linked to a pigmentation deficiency or even pityriasis versicolor, a surficial mycosis causing the appearance of light spots which may appear immediately upon or after exposure to the sun, or even certain pathologies associated with chronologic or actinic aging.

Thus, in another embodiment, the peptides according to the invention, as described previously, can be used to fabricate a medication intended for the treatment of dermatological conditions.

In another embodiment, the present invention concerns a cosmetic procedure for increasing the synthesis of melanin in the melanocytes and promoting the natural pigmentation of the skin and the hair, consisting of applying on the skin or the hair an effective quantity of active agent or of the cosmetic composition containing it, as defined previously, in order to obtain the desired action.

The invention again concerns a cosmetic-treatment procedure designed to prevent or to treat the whitening of hair and fur, consisting of applying, on the skin, the composition as defined previously. a cosmetic-treatment procedure for the care of the skin and/or its appendages consisting of applying onto the surface of the skin an effective quantity of active agent, or of the cosmetic composition containing it, as defined previously, in order to obtain the desired action.

The cosmetic-treatment procedure of the invention can be implemented particularly by applying the cosmetic compositions as defined above, according to the usual technique for using these compositions, for example, application of creams, gels, butters, lotions, milks, shampoos, or sunscreen compositions onto the skin or the hair.

Specific embodiments of this procedure for cosmetic treatment also result from the preceding description. Other advantages and characteristics of the invention will be more apparent upon reading the examples given by way of illustration and non-restrictive.

EXAMPLE 1

Ex Vivo Study of the Effect of the Peptide According to the Invention on the Synthesis of Melanin The aim of this ex vivo study is to highlight the increase in melanization produced by the peptides according to the invention.

Protocol: Biopsies of human skin 6 mm in diameter are held in an ex vivo culture in the presence of a specific medium (1 g/L DMEM, Ham's F-12, SVF, and antibiotics) on inserts deposited on 6-well plates. The biopsies either receive or do not receive two applications daily of the peptide with sequence SEQ ID No. 3 in a concentration of 1% starting with a 50-ppm solution. The duration of the treatment is 48 hours. The biopsies are subsequently fixed in 9% formaldehyde and NaCl (150 mM) for 10 hours and then enclosed in paraffin. Thin-sections of the skin 3 μm thick are then made, and the melanin is specifically stained by the Fontana-Masson technique.

Results: The skin sections which did not receive the application of the compound exhibit a low-intensity coloration. On the other hand, the skin thin-sections which received applications of the peptide with sequence SEQ ID No. 3 exhibit a coloration of clearly increased intensity. Moreover, the melanin is located in the basal layer but is also transported into the supra-basal layers.

Conclusions: The peptide of sequence SEQ ID No. 3 induces a strong increase in the synthesis of melanin by the melanocytes and stimulates the entire process of melanin distribution in the epidermis.

EXAMPLE 2

Preparation of Compositions

1. Protective Sun Cream

| Trade name | International Nomenclature of Cosmetic Ingredients (INCI) name | % by volume |
| --- | --- | --- |
| PHASE A | | |
| Demineralized water | Aqua (water) | In sufficient quantity |
| Pemulen ® TR-1 | Acrylates/C10-30 alkyl acrylate cross-polymer | 0.40 |
| Glycerine | Glycerin | 3.00 |
| Nipastat ® Sodium | Sodium methylparaben (and) sodium ethylparaben (and) sodium butylparaben (and) sodium propylparaben (and) sodium isobutylparaben | 0.15 |
| PHASE B | | |
| Parsol ® MCX | Ethylhexyl methoxycinnamate | 7.50 |
| Eusolex ® 4360 | Benzophenone-3 | 3.00 |
| Parsol ® 1789 | Butyl methoxydibenzoylmethane | 2.00 |
| Myritol ® 318 | Caprylic/capric triglyceride | 4.00 |
| Emulgade ® SEV | Hydrogenated palm glycerides (and) ceteareth-20 (and) ceteareth-12 (and) cetearyl alcohol | 5.00 |
| Propylparaben | Propylparaben | 0.15 |
| Nacol ® 16-98 | Cetyl alcohol | 1.00 |
| PHASE C | | |
| TEA | Triethanolamine | 0.20 |
| PHASE D | | |
| Peptide sequence SEQ ID No. 3 | | 0.1 ppm |
| Perfume | Perfume (fragrance) | In sufficient quantity |
| Colorant | | In sufficient quantity |

The constituents of phase A and of phase B are heated separately between 70° C. and 75° C. Phase B is emulsified in phase A while stirring. Phase C is added, at 45° C., while increasing the stirring. Phase D is finally added when the temperature is below 40° C. Cooling is continued down to 25° C. with brisk stirring.

2. Self-Tanning Cream

| Trade name | INCI name | % by volume |
| --- | --- | --- |
| PHASE A | | |
| Demineralized water | Aqua (water) | In sufficient quantity |
| Dipropylene glycol | Dipropylene glycol | 2.00 |
| Glycerine | Glycerin | 2.00 |
| Glydant Plus ® liquid | DMDM hydantoin (and) iodopropynyl butylcarbamate | 0.40 |
| PHASE B | | |
| Emulgade ® SEV | Glyceryl stearate (and) ceteareth-20/ceteareth-12 (and) cetearyl alcohol (and) cetyl palmitate | 8.00 |
| Lanette ® O | Cetearyl alcohol | 1.50 |
| Cetiol ® V | Decyl oleate | 5.00 |
| DC [Dow Corning]™ 200 | Cyclomethicone | 2.00 |
| Cetiol ® SN | Cetearyl isononanoate | 4.00 |
| Isopropyl palmitate | Isopropyl palmitate | 3.00 |
| Myritol ® 318 | Caprylic/capric triglyceride | 4.00 |
| Tocopheryl acetate | Tocopheryl acetate | 0.50 |
| PHASE C | | |
| Peptide sequence SEQ ID No. 4 | | |
| PHASE D | | |
| Demineralized water | Aqua (water) | 10.00 |
| Dihydroxyacetone | Dihydroxyacetone | 5.00 |
| PHASE E | | |
| Caramel W 8016 colorant | Caramel | 0.02 |
| Perfume | Perfume (fragrance) | In sufficient quantity |

Phases A and B are heated separately while stirring at 75° C. Emulsify phase B into phase A while stirring vigorously. Introduce the peptides below 40° C. Then introduce phase D, which was solubilized in the cold in advance. Color and perfume. Adjust the pH as necessary to 4-4.5.

3. Self-Tanning Spray

| Trade name | INCI name | % by volume |
|---|---|---|
| PHASE A | | |
| Demineralized water | Aqua (water) | In sufficient quantity |
| Propylene glycol | Propylene glycol | 5.00 |
| Glycerine | Glycerin | 2.00 |
| Allantoine | Allantoin | 0.20 |
| PHASE B | | |
| Keltrol ® RD | Xanthan gum | 0.05 |
| PHASE C | | |
| Glydant Plus ® liquid | DMDM hydantoin (and) iodopropynyl butylcarbamate | 0.40 |
| PHASE D | | |
| Peptide sequence SEQ ID No. 3 | | |
| PHASE E | | |
| Dihydroxyacetone | Dihydroxyacetone | 5.00 |
| Demineralized water | Aqua (water) | 10.00 |
| PHASE F | | |
| Caramel E 105C colorant | Caramel | In sufficient quantity |
| Perfume | Perfume (fragrance) | In sufficient quantity |

Prepare phase A while stirring. Incorporate the xanthan gum gradually during dispersant stirring. Phases C and D will be incorporated once the gel has set. Phase E, prepared in advance to the point of perfect DHA dissolution, will then be added. Adjust the pH if necessary to 4-4.5. Color and perfume.

4. After-Sun Milk

| Trade name | INCI name | % by volume |
|---|---|---|
| PHASE A | | |
| Montanov ™ L | C14-22 alcohols (and) C12-20 alkyl glucoside | 3.00 |
| Waglinol 2559 | Cetearyl isononanoate | 4.00 |
| Tegosoft ® TN | C12-15 alkyl benzoate | 3.00 |
| Apricot kernel oil | Prunus armeniaca (apricot) kernel oil | 2.00 |
| Avocado oil | Persea gratissima (avocado) oil | 1.00 |
| Abil ® 350 | Dimethicone | 1.00 |
| PHASE B | | |
| Demineralized water | Aqua (water) | In sufficient quantity |
| PHASE C | | |
| Simulgel ™ EG | Sodium acrylate/acryloyl-dimethyl taurate copolymer (and) isohexadecane (and) polysorbate 80 copolymer (and) polysorbate 80 | 0.4 |
| PHASE D | | |
| Phenonip ® | Phenoxyethanol (and) methylparaben (and) ethylparaben (and) butylparaben (and) propylparaben (and) isobutylparaben Ethylparaben and propylparaben and butylparaben | 0.30 |
| Germall ® 115 | Imidazolidinyl urea | 0.20 |
| PHASE E | | |
| Peptide sequence SEQ ID No. 3 | | 0.5 ppm |

Prepare phase A while stirring. Incorporate the xanthan gum gradually with dispersant stirring. Phases C and D will be incorporated once the gel has set. Phase E, prepared in advance to the point of perfect DHA dissolution, will then be added. Adjust the pH if necessary to 4-4.5. Color and perfume.

The invention claimed is:

1. A cosmetic or pharmaceutical composition, comprising: a peptide fragment of protein SLC24A5; and a physiologically acceptable medium, wherein, said peptide fragment consists of the sequence selected from the group consisting of:

| | |
|---|---|
| Gly-Gly-Leu-Thr-Leu-Leu-Ala-Ala; | (SEQ ID NO: 1) |
| Leu-Thr-Leu-Leu-Ala-Ala; | (SEQ ID NO: 2) |
| Thr-Leu-Leu-Ala; | (SEQ ID NO: 3) |
| Thr-Val-Phe-Ala; | (SEQ ID NO: 4) |
| Thr-Ala-Leu-Ala; and | (SEQ ID NO: 5) |
| Thr-Val-Leu-Ala | (SEQ ID NO: 6). |

2. The composition according to claim 1, wherein said peptide fragment is SEQ ID NO: 3.

3. The composition according to claim 1, wherein said peptide fragment is SEQ ID NO: 4.

4. The composition according to claim 1, wherein said peptide is protected by an acylation or an acetylation of an amino-terminal end, or an amidation or an esterification of a carboxy-terminal end, or both.

5. The composition according to claim 1, wherein said peptide fragment is present in the composition at a concentration between 0.0005 ppm and 500 ppm.

6. The composition according to claim 1, wherein said peptide fragment is solubilized in advance in one or several cosmetically or pharmaceutically acceptable solvents, water, glycerol, ethanol, propylene glycol, butylene glycol, dipropylene glycol, ethoxylated or propoxylated diglycols, cyclic polyols, vaseline, a vegetable oil, or any mixture thereof.

7. The composition according to claim 1, wherein the composition is in a form for topical application, and comprises a cosmetically or dermatologically acceptable medium.

8. The composition according to claim 1, wherein said peptide fragment is present in the composition as an active agent, alone or in association with at least one other active agent.

9. The composition according to claim 1, further comprising at least one exogenous colorant of surface layers of epidermis and/or at least one active pro-pigmenting agent different from said peptide fragment selected from the group consisting of: substrates of tyrosinase, prostaglandins, cAMP activator compounds and pigmenting plant extracts.

10. An isolated peptide fragment of protein SLC2445, wherein,
said peptide fragment consists of the sequence selected from the group consisting of:

| | |
|---|---|
| Gly-Gly-Leu-Thr-Leu-Leu-Ala-Ala; | (SEQ ID NO: 1) |
| Leu-Thr-Leu-Leu-Ala-Ala; | (SEQ ID NO: 2) |
| Thr-Leu-Leu-Ala; | (SEQ ID NO: 3) |
| Thr-Val-Phe-Ala; | (SEQ ID NO: 4) |
| Thr-Ala-Leu-Ala; and | (SEQ ID NO: 5) |
| Thr-Val-Leu-Ala | (SEQ ID NO: 6). |

11. A method of preparing a cosmetic or pharmaceutical composition, comprising mixing a physiologically acceptable medium with at least one peptide fragment according to claim 10.

12. A method of inducing, restoring or stimulating natural pigmentation of skin, fur, or hair, comprising applying a composition to a subject in need thereof, said composition having an effective amount of at least one peptide fragment according to claim 10.

13. A composition to prepare skin for exposure to sun or to protect skin from solar radiation, comprising:
at least one active principle designed to prepare the skin for exposure to the sun or to protect the skin from solar radiation; and
at least one peptide fragment according to claim 10.

14. A composition to protect skin against external aggression, comprising at least one peptide fragment according to claim 10 in an amount effective to protect the skin against external aggression.

15. A pharmaceutical composition to alleviate a skin pigmentation disorder or vitiligo, comprising:
a pharmaceutically acceptable medium; and
at least one peptide fragment according to claim 10.

16. A composition to inhibit or treat whitening of fur and/or hair, comprising:
at least one compound that promotes pigmentation of fur or hair; and
at least one peptide fragment according to claim 10.

17. A method of increasing melanization, comprising applying topically on area to be treated of a subject an effective amount of at least one peptide fragment according to claim 10.

18. A method of preparing skin for exposure to sun or protecting skin from solar radiation, comprising applying a composition to the skin of a subject in need thereof, said composition comprising:
at least one peptide fragment according to claim 10; and
at least one active principle designed to prepare the skin for exposure to the sun or to protect the skin from solar radiation.

19. A method of alleviating a skin pigmentation disorder or vitiligo, comprising administering a pharmaceutical composition to a subject in need thereof, said composition comprising:
at least one peptide fragment according to claim 10; and
a pharmaceutically acceptable medium.

20. A method of inhibiting or treating whitening of fur and/or hair, comprising administering a composition to a subject in need thereof, said composition comprising:
at least one peptide fragment according to claim 10; and
at least one compound that promotes pigmentation of fur or hair.

* * * * *